United States Patent

Van Geenen et al.

[11] Patent Number: 4,692,520
[45] Date of Patent: Sep. 8, 1987

[54] N-SUBSTITUTED ACYL-LACTAM COMPOUND

[75] Inventors: Albert A. Van Geenen, Brunssum; Jozef J. M. Bongers, Elsloo (L.), both of Netherlands

[73] Assignee: Stamicarbon B.V. (Subsidiary of DSM), Geleen, Netherlands

[21] Appl. No.: 808,559

[22] Filed: Dec. 13, 1985

[30] Foreign Application Priority Data

Dec. 20, 1984 [NL] Netherlands .......................... 8403860

[51] Int. Cl.$^4$ .......................................... C07D 223/10
[52] U.S. Cl. ..................... 540/451; 546/221; 546/243; 548/538; 548/540; 525/315; 540/529
[58] Field of Search ................. 260/239.3 R; 546/243, 546/221; 548/538, 540; 540/531, 451, 529

[56] References Cited

U.S. PATENT DOCUMENTS 4,590,243  5/1986  Gabbert et al. ...................... 525/184
4,626,385  12/1986 Ashida et al. ........................ 540/451

Primary Examiner—Robert T. Bond
Attorney, Agent, or Firm—Cushman, Darby & Cushman

[57] ABSTRACT

The invention relates to the N-substituted acyl-lactam compound of the formula:

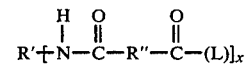

where
R' is a bivalent cyclic or non-cyclic alkyl, aralkyl, alkaryl or aryl radical
R" a bivalent radical having the following general formula

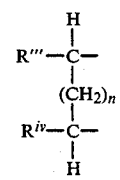

wherein
R''' is H, alkyl, cycloalkyl, aryl, alkaryl or aralkyl,
R$^{iv}$ is H, alkyl, cycloalkyl, aryl, alkaryl or aralkyl where R''' and R$^{iv}$ may jointly form a substituted or non-substituted cycloalkyl residue
n is 0 or 1
(-L) represents a non-opened lactam ring and
x a number >1.

It has been found that this group of compounds is very suitable as activator in the preparation of nylon polymers, more specifically in the so-called RIM (Reaction Injection Moulding) or RRIM (reinforced RIM) systems, in which it is highly essential for the polymerization to take effect within a very short time.

11 Claims, No Drawings

N-SUBSTITUTED ACYL-LACTAM COMPOUND

FIELD OF THE INVENTION

The invention relates to an N-substituted acyl-lactam compound. In the anionic polymerization of lactams, such as caprolactam, N-substituted acyl-lactam compounds are suitable accelerators. These compounds can be used particularly in the preparation of RIM (=Reaction Injection Moulding) nylon on account of the short time required for their reaction, which makes it possible for lactam to be polymerized in a mould.

BACKGROUND OF THE PRESENT INVENTION

The RIM preparation process is a one-step process in which the liquid components are put in a mould, upon which a very rapid polymerization takes place resulting in a plastic article. The pressures applied in that process are much lower than in the much used injection moulding process.

In a RIM preparation process the viscosity of the components put in the moulds is 50 to 10,000 cps, preferably about 1000–3000 cps. In that process the temperature of the components ranges from room temperature for urethanes to about 100°–150° C. for lactams. The mould temperature in a RIM preparation process for lactam is usually between 100° and 220° C. The pressures applied range from 1 to 100 bar, preferably from 1 to 30 bar.

For smaller articles the reaction in the mould must be finished in less than 5 minutes.

The polymerization of a lactam to form nylon has been known for long.

In the U.S. Pat. No. 3,018,273 a process for the anionic polymerization of caprolactam is described using an organomagnesium compound as catalyst and an N-N diacyl compound as activator.

The British Pat. No. 1,067,153 describes a process for preparing nylon block copolymers by polymerizing caprolactam in the presence of various kinds of activators. In the example the use of an isocyanate-terminated polypropylene glycol as activator and of a potassium compound as catalyst is described.

In the U.S. Pat. Nos. 3,862,262, 4,031,164, 4,034,015, 4,223,112, 3,925,325 and 3,965,375, as well as Reissue patent U.S. Pat. No. Re. 30,371, various aspects of the preparation of activators for the polymerization of lactam and of the polymerization of lactam itself are described.

The U.S. Pat. Nos. 4,031,164 and 4,223,112 describe lactam-polyol polyacyl-lactam block copolymers with specific ratios of the various components.

The U.S. Pat. No. 3,862,262 describes lactam-polyol-acyl-polylactam block copolymers.

The U.S. Pat. No. 4,034,015 aims at nylon block copolymers with at least 5% ester end groups.

The other patents mentioned relate to the preparation of ester-amide compounds by condensation of alcohol and acyl-lactam in the presence of various kinds of catalysts.

The European patent application Nos. 67693, 67694 and 67695 laid open to public inspection relate to acyl-halide and acyl-lactam compounds and to a process for preparing nylon block copolymers with these. The acyl-halide and acyl-lactam compounds are described by means of complex formulas.

The U.S. Pat. No. 3,366,608 describes the reaction of an N,N' diacyl-bis caprolactam, such as N,N' sebacoyl-bis-caprolactam, a polyol and a basic catalyst. In that process a nylon block copolymer is obtained.

The German patent application no. 2026672 laid open to public inspection describes the use of polyol-containing polyamides for the production of metallized articles. The polyol-containing polyamides are obtained by anionic polymerization of lactam in the presence of a polyol, a basic lactam catalyst and an activator, such as a diisocyanate.

The U.S. Pat. No. 4,540,516 describes the preparation of N-substituted carbamoyl lactam compounds, while the U.S. Pat. No. 4,540,515 describes the use of such a compound for the preparation of nylon block copolymers.

The European patent application no. 147792 describes the catalytic condensation of imides and alcohols to form esteracyllactam and esteramide-acyl-lactam compounds.

In the U.S. Pat. No. 3,704,280 a process is described for the anionic catalytic polymerization of lactam in the presence of a polyether, in which process the activator used is an isocyanate compound.

SUMMARY OBJECTS OF THE PRESENT INVENTION

The invention relates to N-substituted acyl lactam compounds of the formula:

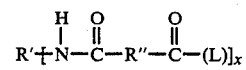

where
R' is a bivalent cyclic or non-cyclic alkyl, aralkyl or aryl radical,
R" is a bivalent radical having the following formula:

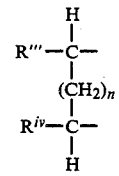

wherein:
R'" is H, alkyl, cycloalkyl, aryl, or aralkyl,
R$^{iv}$ is H, alkyl, cycloalkyl, aryl, alkaryl, or aralkyl, or R'" and R$^{iv}$ may, together with the carbon atom to which each is bonded, jointly form a substituted or non-substituted cycloalkyl residue,
n is 0 or 1,
(L) represents an unopened lactam ring and
x is a number equal to or greater than 1.

The compounds produced by the process are very suitable for use as activators in the preparation of nylon block copolymers, and more specifically in RIM or RRIM systems.

The present invention provides a novel process for acyl-lactam compound that can well be used, inter alia, as an accelerator for anionic polymerization of lactam as may be applied, for instance, in (rotational) moulding of nylon. The present invention thus also provides a novel acyl-lactam compound capable of producing nylon polymers with good properties, particularly via 'Reaction Injection Moulding'.

DETAILED DESCRIPTION OF THE PRESENT INVENTION

The N-substituted acyl-lactam compound according to the invention is characterized by the formula:

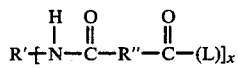

where
- R' is a bivalent cyclic or non-cyclic alkyl, aralkyl, alkaryl or aryl radical
- R'' a bivalent radical having the following general formula

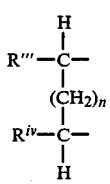

wherein
- R''' is H, alkyl, cycloalkyl, aryl, alkaryl or aralkyl,
- R$^{iv}$ is H, alkyl, cycloalkyl, aryl, alkaryl or aralkyl
where
- R''' and R$^{iv}$ may jointly form a substituted or non-substituted cycloalkyl residue
- n is 0 or 1
- (-L) represents a non-opened lactam ring of the formula

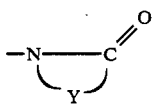

wherein Y is a hydrocarbon residue with 3–11 carbon atoms, and x is a number ≧1.

It has been found that this group of compounds is very suitable as activator in the preparation of nylon polymers, more specifically in the so-called RIM (Reaction Injection Moulding) or RRIM (reinforced RIM) systems, in which it is highly essential for the polymerization to take effect within a very short time.

The compounds according to the invention can be prepared by reacting the reaction product of a lactam with a dicarboxylic acid anhydride in a liquid state at a temperature of at most 150° C. and preferably at a temperature between 30° C. and 140° C. with an isocyanate or polyisocyanate. Liquid state is understood to mean a mixture of two liquids as well as a solid component dissolved in a liquid component.

The reaction product (I) of a lactam with a dicarboxylic acid anhydride is understood to comprise compounds with the formula

where
- R'' is a bivalent radical having the following general formula

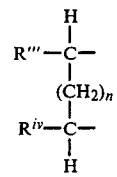

wherein
- R''' is H, alkyl, cycloalkyl, aryl, alkaryl or aralkyl,
- R$^{iv}$ is H, alkyl, cycloalkyl, aryl, alkaryl or aralkyl/- where
- R''' and R$^{iv}$ may jointly form a substituted or non-substituted cycloalkyl residue
- n is 0 or 1 and
- (-L) represents a non-opened lactam ring of the formula

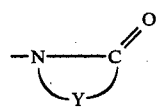

wherein Y is a hydrocarbon residu with 3–11 carbon atoms.

This reaction product (I) is formed when a dicarboxylic acid anhydride and a lactam are reacted with each other in a liquid state at a temperature of 150° C. at most, preferably at a temperature between 70° C. and 140° C. and more preferably between 90° C. and 130° C.

If reaction product (I) and an isocyanate or polyisocyanate are brought together, the N-substituted acyllactam compounds according to the present invention will be formed while carbon dioxide is being separated off.

Various isocyanates and polyisocyanates are suitable for use in the present invention. These may be aliphatic, araliphatic, cycloaliphatic and aromatic isocyanates.

Examples of suitable isocyanates are butylisocyanate, phenylisocyanate, 1,5-hexanediisocyanate, 1,6-hexanediisocyanate, xylylenediisocyanate (XDI), isophoronediisocyanate, toluenediisocyanate (TDI), 4,4'-diphenylmethanediisocyanate (MDI) and hydrogenated TDI, XDI or MDI, modified MDI (e.g. with carbodiimide).

As lactam various lactams may be used, such as 2-pyrrolidone, 2-piperidone, enantholactam, decanolactam, undecanolactam, lauryllactam and caprolactam, but also substituted lactams, or mixtures of two or more lactams.

More specifically caprolactam is used.

The dicarboxylic acid anhydrides to be used are chosen from the group of dicarboxylic acid anhydrides having the following general formula

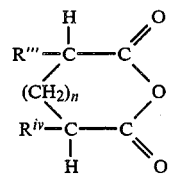

where
- R''' represents H, alkyl, cycloalkyl, aryl, alkaryl or aralkyl $R^{iv}$ is H, alkyl, cycloalkyl, aryl, alkaryl or aralkyl where $R'''$ and $R^{iv}$ may jointly form a substituted or non-substituted cycloalkyl residue, and n is 0 or 1.

Very suitable are dicarboxylic acid anhydrides, such as glutaric acid anhydride, succinic acid anhydride, and saturated alicyclic 1,2-dicarboxylic acid anhydrides, such as 1,2-cyclohexanedicarboxylic acid anhydride.

Applicant has found that compounds like maleic acid anhydride and phthalic acid anhydride cannot be used in the present invention.

The present invention also relates to a process for preparing a nylon polymer, as well as to an article wholly or partly produced from such a nylon copolymer.

This process is characterized in that an N-substituted acyl-lactam compound described above is reacted in melted lactam to form a nylon polymer in the presence of a lactam polymerization catalyst. Preference is given to carrying out the reaction with an alkali or alkaline earth metal lactamate or with compounds forming alkali or alkaline earth alkali metal lactamate. Examples thereof include potassium lactamate and lactam magnesiumbromide. Already a small amount of catalyst will suffice, for instance less than 1 mole % calculated on the lactam to be polymerized, but larger amounts, to for instance 3 moles % can also be used. Preferably the amount of catalyst is between 0.2 and 3 moles %.

The polymer is formed in a short time, for instance in less than 10 minutes, more specifically between 10 s and 5 minutes, under mild conditions in respect of temperature and pressure.

In the preparation of nylon polymer the object is for the number-average molecular weight of the nylon blocks to be at least 2000, more specifically at least 4000. This can be achieved by varying the number of acyl lactam groups originating from the acyl lactam compound in respect of the amount of lactam added. Preferably from 0.1 mole % to 3 moles %.

The chosen lactam added for preparing the nylon polymer is preferably the same as used in the acyl lactam compound. More specifically caprolactam is used.

In the preparation of the nylon polymer it may be essential for the polymerization to be carried out in the presence of one or more compounds that are normally used in nylon polymers such as fillers, softeners, flame-retardants, stabilizers, impact modifiers and reinforcing fibres, such as asbestos or glass fibres.

The present invention is elucidated hereinafter by means of a few examples.

EXAMpLE 1

28.5 g (0.25 mole) glutaric acid anhydride and 28.25 g (0.25 mole) ε-caprolactam were reacted for 4 hours at 125° C.

To the reaction product formed 21 g (0.125 mole) hexamethylenediisocyanate was added gradually in 1 hour at 110° C. Immediately after the first addition $CO_2$ formation was observed. After complete addition the whole was after-reacted under vacuum for 1 hour at 125° C.

After bringing together a solution of 1.7 g of the resulting reaction product in 16 g caprolactam and a solution of 0.7 g lactam magnesiumbromide in 20 g caprolactam a solid nylon polymer was formed in 4 min. and 10 sec at 130° C.

EXAMPLE 2

According to the process described in example 1 an acyl-lactam compound was synthesized from 25 g succinic acid anhydride (0.25 mole) 28.25 g ε-caprolactam and 27.3 g isophoronediisocyanate.

1.8 g of the resulting reaction product was dissolved at 100° C. in 18 g caprolactam.

After bringing this solution together with a solution of 1.4 g lactammagnesiumbromide in 18.7 g caprolactam a solid nylon polymer was obtained after 3 min. and 40 sec. at 130° C.

EXAMPLE 3

According to the process described in example 1 an acyl-lactam compound was prepared from 38.5 g (0.25 mole) 1.2 cyclohexanedicarboxylic acid anhydride, 28.25 g ε-caprolactam and 27.3 g isophoronediisocyanate. 2.0 g of the resulting reaction product was dissolved at 100° C. in 18 g caprolactam.

After bringing this solution together with a solution of 0.9 g potassium lactamate in 20 g caprolactam a solid nylon polymer was obtained at 130° C. after 2 min. and 50 sec.

We claim:

1. N-substituted acyl-lactam compound having the formula

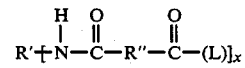

wherein
  R' is a bivalent alkyl, aralkyl, alkaryl or aryl residue radical of a polyisocyanate,
  R" is a bivalent radical of a dicarboxylic acid anhydride having the following formula

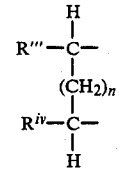

wherein
  $R'''$ is H, alkyl, cycloalkyl, aryl, alkaryl or aralkyl,
  $R^{iv}$ is H, alkyl, cycloalkyl, aryl, alkaryl or aralkyl, where
  $R'''$ and $R^{iv}$, together with the carbon atom to which each is bonded, may jointly form a cycloalkyl residue,
  n is 0 or 1,
  (L) represents a non-opened lactam ring having the formula

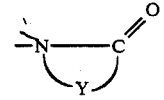

wherein
  Y has 3–11 carbon atoms, and X is a number ≧ to 1.

2. Compound according to claim 1, wherein R' is the residue of butylisocyanate, phenylisocyanate, 1,5-hexanediisocyanate, 1,6-hexanediisocyanate, isophoronediisocyanate, toluenediisocyanate, MDI, hydrogenated MDI, modified MDI and xylylenediisocyanate.

3. Compound according to claim 1, wherein R'' is the residue of glutaric acid anhydride, succinic acid anhydride or 1,2 cyclo-hexanedicarboxylic acid anhydride.

4. Process for preparing an N-substituted acyl-lactam compound comprising:
reacting the reaction product of a lactam with a dicarboxylic acid anhydride at a temperature of at most 150° C. with an isocyanate or a polyisocyanate.

5. Process according to claim 4, wherein said isocyanate is selected from the group consisting of butylisocyanate, phenylisocyanate, 1,5-hexanediisocyanate, 1,6-hexanediisocyanate, isophoronediisocyanate, toluenediisocyanate, MDI, hydrogenated MDI, modified MDI xylylenediisocyanate, hydrogenated toluenediisocyanate and hydrogenated xylylenediisocyanate.

6. Process according to claim 4, wherein said dicarboxylic acid anhydride is selected from the group consisting of glutaric acid anhydride, succinic acid anhydride and 1,2-cyclohexanedicarboxylic acid anhydride.

7. A compound according to claim 3, wherein R' is the residue of butylisocyanate, phenylisocyanate, 1,5-hexanediisocyanate, 1,6-hexanediisocyanate, isophoronediisocyanate, toluenediisocyanate, MDI, hydrogenated MDI, modified MDI, xylylenediisocyanate, hydrogenated toluendiisocyanate, and hydogenated xylylenediisocyanate.

8. A compound according to claim 7, wherein the lactam of said non-opened lactam ring is selected from the group consisting of 2-pyrrolidone, 2-piperidone, enatholactam, decanolactam, undecanolactam, lauryllactam, caprolactam and mixtures thereof.

9. Process according to claim 5 wherein the dicarboxylic acid anhydride is selected from the group consisting of glutaric acid anyhydride, succinic acid anyhydride and 1,2-cyclohexanedicarboxylic acid anhydride.

10. Process according to claim 9, wherein said process is conducted in the liquid state at a temperature between 30° C. and 140° C.

11. Process according to claim 9, wherein said lactam is selected from the group consisting of 2-pyrrolidone, 2-piperidone, enantholactam, decanolactam, undecanolactam, lauryllactam, caprolactam and mixtures thereof.

* * * * *